United States Patent [19]

Albrecht et al.

[11] 3,954,983

[45] May 4, 1976

[54] TRIAZOLOBENZOCYCLOALKYLTHIADIA-ZINE DERIVATIVES

[75] Inventors: William L. Albrecht; Francis W. Sweet, both of Cincinnati, Ohio

[73] Assignee: Richardson-Merrell Inc., Wilton, Conn.

[22] Filed: Apr. 28, 1975

[21] Appl. No.: 571,941

[52] U.S. Cl.............................. 424/246; 260/243 R
[51] Int. Cl.² ................................... C07D 285/20
[58] Field of Search................. 260/243 R; 424/246

[56] References Cited
OTHER PUBLICATIONS

George et al., *J. Med. Chem.*, Vol. 14, pp. 335–338 (1971).

*Primary Examiner*—John M. Ford
*Attorney, Agent, or Firm*—William J. Stein; Eugene O. Retter; George W. Rauchfuss, Jr.

[57] ABSTRACT

Novel triazolobenzocycloalkylthiadiazines, their preparation, and use as central nervous system antidepressants.

10 Claims, No Drawings

TRIAZOLOBENZOCYCLOALKYLTHIADIAZINE DERIVATIVES

SUMMARY OF THE INVENTION

This invention relates to new triazolobenzocycloalkylthiadiazines, their method of preparation, compositions thereof, and their usefulness as pharmaceutical agents. More particularly, the novel compounds of this invention are derivatives of triazolobenzocycloalkylthiadiazines, which can be represented by the following structural formula:

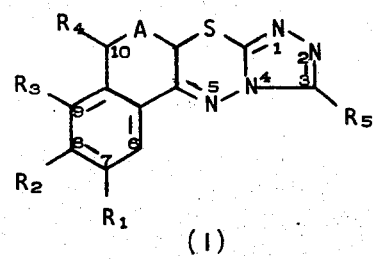

wherein $R_1$, $R_2$ and $R_3$ are each selected from the group consisting of hydrogen, lower alkyl having from 1 to 4 carbon atoms, inclusively, and lower alkoxy having from 1 to 4 carbon atoms, inclusively; $R_4$ is selected from the group consisting of hydrogen and lower alkyl having from 1 to 4 carbon atoms, inclusively; A is a sigma bond or the methylene radical; $R_5$ is lower alkyl having from 1 to 4 carbon atoms, inclusively; and the pharmaceutically acceptable acid addition salts thereof.

In general, the triazolobenzocycloalkylthiadiazine derivatives described herein are prepared by reacting in solution a 2-halobenzocycloalkan-1-one with a 4-amino-4H-1,2,4-triazole-3-thiol. This reaction can be schematically represented as follows:

I is administered to an animal in need thereof. Various compositions including convenient dosage unit forms are also described herein.

BACKGROUND OF THE INVENTION

Fluctuations in mood, either in the direction of excitement, elation and euphoria, or contrariwise in the direction of unhappiness, malaise and depression, are of common occurrence in the ordinary individual. Normal changes in the upwards directions are rarely of such a degree as to necessitate medical attention. However, fluctuations in the depressive direction may be of a frequency or a magnitude as to require medical attention.

The compounds of the present invention have been observed to selectively remit reserpine extrapyramidal motor deficiencies. Thus, they are useful as central nervous system stimulants, mood elevators and psychic energizers in the treatment of depressed mental health conditions. Similarly, the compounds of this invention are useful in the treatment of catalepsy and Parkinsonian-like effects resulting from the administration of certain neuroleptic agents.

The closest art known to applicants discloses a series of 5-alkyl-4-amino-s-triazole-3-thiols stated to have analgetic and antiinflammatory activities, George et al., J. Med. Chem. 14, 335 (1971). Disclosed therein are four compounds containing a triazolothiadiazine nuclear moiety. These compounds, however, lack the additional benzocycloalkyl portion of the nucleus necessary for the compounds of the present invention. Moreover, the prior art compounds possess completely different pharmacological properties from those properties described for the compounds of this invention.

DETAILED DESCRIPTION OF THE INVENTION

As can be seen from general formula (I) and its description above, the compounds of the present invention include two closely related groups of compounds which differ only in the size of the cycloalkyl moiety of the ring nucleus. Thus, the cycloalkyl ring may be either a 5 or a 6-membered ring as indicated by the symbol A, which can be either a sigma bond or the methylene radical.

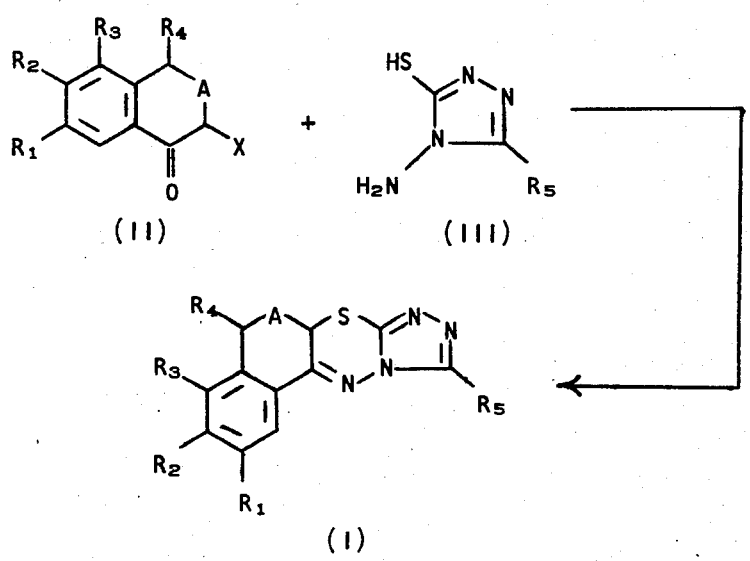

In the above reaction sequence the symbols $R_1$, $R_2$, $R_3$, $R_4$, $R_5$ and A have the values previously assigned and X is a halogen selected from the group consisting of chlorine, bromine and iodine.

In order to achieve an antidepressant effect, a therapeutically effective amount of a compound of formula When A is a sigma bond, a 5-membered cycloalkyl moiety of the ring nucleus is delineated. The expression "sigma bond" refers to the ordinary single bond linkage between two adjacent carbon atoms resulting from the overlap of their corresponding orbitals. When the symbol A represents a sigma bond, a preferred subgeneric class of triazolobenzocycloalkylthiadiazine derivatives is delineated as illustrated by the following structural formula:

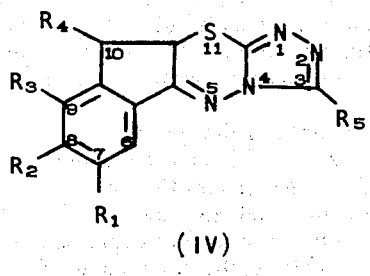

(IV)

For purposes of nomenclature, the bridged phenylcyclopentane portion of the ring nucleus is referred to as a 10,10a-dihydroindeno moiety, and the complete ring nucleus is defined as a 10,10a-dihydroindeno[1,2-e]-s-triazolo[3,4-b][1,3,4]thiadiazine nucleus.

Alternativey, when A is the methylene radical, a 6-membered cycloalkyl moiety is delineated. Thus, when A is the methylene radical, a second preferred subgeneric class of triazolobenzocycloalkylthiadiazine derivatives is described which can be illustrated by the following structural formula:

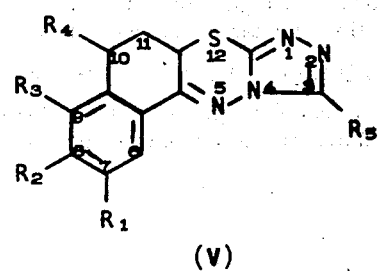

(V)

For purposes of nomenclature, the bridged phenylcyclohexane portion of the ring nucleus is referred to as a 11,11a-dihydro-10H-naphtho moiety, and the complete ring nucleus is defined as a 11,11a-dihydra-10H-naphtho[1,2-e]-s-traizolo[3,4-b][1,3,4]thiadiazine nucleus.

In addition, the triazolobenzocycloalkylthiadiazine derivatives of the present invention can be either substituted or unsubstituted in both the triazole and the 10,10a-dihydroindeno or 11,11a-dihydro-10H-naphtho portions of the ring nucleus. Thus, both groups of compounds can be substituted in the benzenoid portion of the triazolobenzocycloalkylthiadiazine nucleus as indicated by the symbols $R_1$, $R_2$ and $R_3$. When the symbols $R_1$, $R_2$ and $R_3$ are each hydrogen, the benzene ring is, of course, unsubstituted in the 7, 8 9-positions as indicated in formula (I) above. Alternatively, the benzenoid ring may be either mono, di or tri-substituted as illustrated by the representation of the symbols $R_1$, $R_2$ and $R_3$ as either lower alkyl or lower alkoxy. The term "lower alkyl" refers to a univalent, aliphatic carbon side-chain comprising such radicals as methyl, ethyl, propyl, isopropyl, butyl, isobutyl, or t-butyl. The term "lower alkoxy" refers to the corresponding lower alkyl ether derivatives thereof.

As further indicated in formula (I) above, the 10-position of the cyclopentane or cyclohexane ring may also be substituted or unsubstituted. Substitution other than with hydrogen, however, is limited solely to the same lower akyl groups previously defined.

Lastly, the triazole ring may remain unsubstituted or it can be mono-substituted at the 3-position with a variety of substituents as indicated by the symbol $R_5$. Thus, $R_5$ may represent an alkyl group containing from 1 to 15 carbon atoms. In addition to the specific lower alkyl groups previously mentioned, this group includes such radicals as amyl, hexyl, heptyl, octyl, nonyl, decyl, undecyl, dodecyl, tridecyl, tetradecyl and pentadecyl. Additionally, the various branched and positional isomers can be included as long as the alkyl group is univalent and is not in excess of 15 carbon atoms. The symbol $R_5$ may also represent a univalent cycloalkyl group having from 3 to 6 carbon atoms. Illustrative of such groups are the cyclopropyl, cyclobutyl, cyclopentyl and cyclohexyl radicals. Univalent alkyl ethers can also be represented by the symbol $R_5$. These ether moieties which are aliphatic in nature and which contain a combined carbon content ranging from 2 to 8 carbon atoms, include such members as methoxymethyl, methoxyisopropyl, methoxyheptyl, ethoxyethyl, ethoxyhexyl, propoxypropyl, propoxyisobutyl, isobutoxymethyl, amyloxymethyl, hexyloxyethyl and isoheptyloxymethyl. The preferred substituents at the 3-position of the triazole nucleus are the lower alkyl radicals having from 1 to 4 carbon atoms as previously described.

The expression "pharmaceutically acceptable acid addition salts" is intended to apply to any non-toxic inorganic or organic acid addition salts of the base compounds represented by formula (I) above. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di and tricarboxylic acids. Such acids include, for example, acetic, glycolic, lactic, pyruvic, malonic, succinic, glutaric, fumaric, malic, tartaric, citric, ascorbic, maleic, benzoic, p-hydroxybenzoic, phenylacetic, cinnamic, salicylic, 2-phenoxybenzoic and sulfonic acids such as methane sulfonic acid and 2-hydroxyethane sulfonic acid. Due to the fact that the triazolobenzocycloalkylthiadiazines are relatively weak organic bases, the salts formed by the addition of strong inorganic mineral acids are more readily isolated and represent the preferred salts of this invention. In addition to salt formation, the free base compounds of this invention may exist in either a hydrated or a substantially anhydrous form. Generally speaking, the acid addition salts of these compounds are crystalline materials which are soluble in water and various hydrophilic organic solvents and in comparison to their free base forms, generally demonstrate a higher melting point and an increased chemical stability.

Illustrative of the specific base compounds which are encompassed by the formula (I) above are:
  10,10a-dihydro-3,7-dimethyl-indeno[1,2-e]-s-triazolo[3,4-b][1,3,4]thiadiazine,
  8-ethyl-10,10a-dihydro-3-propyl-indeno[1,2-e]-s-triazolo[3,4-b][1,3,4]thiadiazine, 10,10a-dihydro-3-methyl-9-propyl-indeno[1,2-e]-s-triazolo[3,4-b][1,3,4]thiadiazine,
10,10a-dihydro-3,10-dipropyl-indeno[1,2-e]-s-triazolo[3,4-b][1,3,4]thiadiazine,
3-t-butyl-10,10a-dihydro-7,8-dimethyl-indeno[1,2-e]-s-triazolo[3,4-b][1,3,4]thiadiazine,
7,8,9-triethyl-10,10a-dihydro-3-isopropyl-indeno[1,2-e]-s-triazolo[3,4-b][1,3,4]thiadiazine,
10,10a-dihydro-7,8-dimethoxy-3-methyl-indeno[1,2-e]-s-triazolo[3,4-b][1,3,4]thiadiazine,
3-butyl-10-ethyl-10,10a-dihydro-indeno[1,2-e]-s-triazolo[3,4-b][1,3,4]thiadiazine,
7,10-dimethyl-10,10a-dihydro-3-isobutyl-indeno[1,2-e]-s-triazolo[3,4-b][1,3,4]thiadiazine,
10,10a-dihydro-3,8,10-trimethyl-indeno[1,2-e]-s-triazolo[3,4-b][1,3,4]thiadiazine,
3-ethyl-11,11a-dihydro-7-methyl-10H-naphtho[1,2-e]-s-thiazolo[3,4-b][1,3,4]thiadiazine,
8-butyl-11,11a-dihydro-3-methyl-10H-naphtho[1,2-e]-s-thiazolo[3,4-b][1,3,4]thiadiazine,
8,9-diethyl-11,11a-dihydro-3-isobutyl-10H-naphtho[1,2-e]-s-thiazolo[3,4-b][1,3,4]thiadiazine,
8-ethoxy-11,11a-dihydro-3-propyl-10H-naphtho[1,2-e]-s-triazolo[3,4-b][1,3,4]thiadiazine,
3-butyl-11,11a-dihydro-10-propyl-10H-naphtho[1,2-e]-s-triazolo[3,4-b][1,3,4]thiadiazine,
7,8,10-triethyl-11,11a-dihydro-3-isopropyl-10H-naphtho[1,2-e]-s-triazolo[3,4-b][1,3,4]thiadiazine,
11,11a-dihydro-3,8,9,10-tetramethyl-10H-naphtho[1,2-e]-s-triazolo[3,4-b][1,3,4]thiadiazine,
9,10-diethyl-11,11a-dihydro-3-propyl-10H-naphtho[1,2-e]-s-triazolo[3,4-b][1,3,4]thiadiazine,
3-ethyl-11,11a-dihydro-7-methoxy-10H-naphtho[1,2-e]-s-triazolo[3,4-b][1,3,4]thiadiazine, and
3-butyl-11,11a-dihydro-8,10-diisopropyl-10H-naphtho[1,2-e]-s-triazolo[3,4-b][1,3,4]thiadiazine The starting materials used for the preparation of the compounds of the present invention are either commercially available or are prepared by a standard or a well-known specific procedure. Thus, the 4-amino-4H-1,2,4-triazole-3-thiols of formula (III) above can be prepared by the reaction of thiocarbohydrazide with an appropriate carboxylic acid or substituted carboxylic acid in accordance with the following reaction scheme:

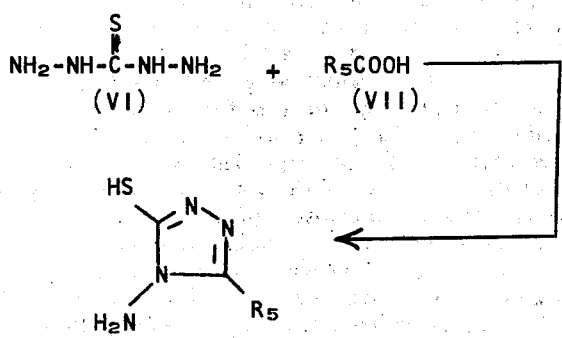

wherein $R_5$ is as previously defined. In general, thiocarbohydrazide and the carboxylic acid are heated together at temperatures ranging from about 100° C. to about 160° C. in the presence or absence of a solvent for a period of from about 1 to about 12 hours. The resulting triazole can then be recovered using standard methods known to those skilled in the art.

The 2-halobenzocycloalkan-1-ones of formula (II) are members of the class of 2-halobenzocyclopentan-1-ones and 2-halobenzocyclohexan-1-ones. These compounds are hereinafter referred to by their trivial names as 2-halo-1-indanones and 2-halo-1-tetralones, respectively. The 2-halo-1-indanones and 2-halo-1-tetralones are either commercially available or can be readily prepared via the halogenation of the corresponding 1-indanones and 1-tetralones, which are also either commercially available or are known compounds. Suitable halogenating agents include bromine, chlorine, cupric bromide and sulfuryl chloride. The 2-iodo-1-indanones and 2-iodo-1-tetralones are prepared via a halogen interchange treating the corresponding 2-chloro or 2-bromo-1-indanones and 2-chloro or 2-bromo-1-tetralones with sodium or potassium iodide in an acetone solution.

The compounds of the present invention are readily obtained by the condensation of the various 2-halobenzocycloalkan-1-ones of formula (II) with the various 4-amino-4H-1,2,4-triazole-3-thiols of formula (III). In general, condensation is achieved by reacting the compounds at an elevated temperature. In those instances where either one or both of the reactants are liquid, condensation can be achieved by simple admixture and subsequent heating. Alternatively, the reaction takes place in a suitable inert solvent. Suitable non-reactive solvents include the lower alkanols, cloroform, dioxane, diethyl ether, tetrahydrofuran, pentane, hexane, heptane, benzene and toluene. The preferred solvents include those lower alkanols having from 1 to 6 carbon atoms including such solvents as methanol, ethanol, isopropanol, amyl alcohol and n-hexanol, with ethanol representing the solvent of choice.

The temperature at which condensation takes place varies from about room temperature to about 150° C. Preferably, the condensation is conducted at temperatures ranging from about 60° C. to about 100° C. in order to obtain maximum yields. As a matter of convenience, the reflux temperature of the reaction mixture is frequently employed.

The reaction time is partly a function of the temperature employed, and partly a function of the degree of stearic hindrance which is encountered. In addition, the nature of the various substituents on the 2-halobenzocycloalkan-1-one and the triazole may necessitate adjustment of the reaction. Generally, however, a reaction time of from about 1 hour to about 12 hours is sufficient for condensation to occur. Preferably, the reaction is conducted from about 1 to 2 hours in order to minimize any thermal degradation that may take place.

The desired products of this invention are generally isolated by concentrating the reaction mixture in vacuo to form an oil or a solid residue. This residue can then be dissolved in an organic solvent such as chloroform or methylene chloride and purified by extraction with an aqueous alkaline solution, such as a 5 or 10% sodium hydroxide solution, in order to remove impurities and any unreacted starting materials. The organic extract which remains can be washed, dried and concentrated to obtain the desired product as a crude material. These crude products can be further purified in a standard manner by recrystallization from ordinary solvents and solvent mixtures including methanol, ethanol, ethyl acetate, methylene chloride, hexane and pentane. The pharmaceutically acceptable acid addition salts can be prepared by recrystallization of the base compounds from an acidified solvent, as for example an ethanolic solution of hydrogen chloride.

The compounds of this invention and their non-toxic pharmacologically acceptable acid addition salts, have useful pharmacodynamic properties. These compounds selectively remit reserpine induced extrapyramidal motor deficits or catalepsy induced in experimental animals. Thus, the instant compounds are useful as antidepressants, antiparkinson agents and useful for the treatment of catalepsy and Parkinsonian-like effects resulting from the administration of neuroleptic agents to mammals in need thereof, as for example, mice, rats, guinea pigs, gerbils, ferrets, dogs, cats, cows, horses, and humans.

The administration of reserpine to mice, rats, cats and dogs results in motor disturbances of extrapyramidal origin which are generally referred to as cataleptic disturbances. Additionally, there results symptoms which resemble those of Parkinson's disease, that is, alkinesia, rigidity and tremors. This response is not uniform in dogs and cats, but rather varies from a moderate tremor and ataxia on the one hand to collapse resembling sleep on the other hand depending upon the particular dosage administered. In addition, there is a peripheral effect as evidenced in mice and rats by paralysis of the eyelid or ptosis, and in cats a paralysis of the nictitating membrane.

The ability of the compounds of this invention to selectively remit reserpine-induced catalepsy, or motor deficits, is demonstrated by a reproducible restoration of motor activity without concurrent remission of the peripheral effects of reserpine ptosis in rats and mice.

For pharmaceutical purposes, the compounds of this invention can be administered to warm-blooded animals perorally or parenterally as active ingredients in customary dosage unit compositions. These compositions consist essentially of a dosage unit form containing the active ingredient and an inert pharmaceutical carrier. Dosage unit forms contemplated by the present invention include tablets, coated pills, capsules, dragees, lozenges, wafers, powders, elixers, clear liquid solutions, suspensions, emulsions, syrups, and parenteral compositions such as intramuscular, intravenous or intradermal preparations. The quantity of active ingredient administered in such dosage forms can vary over a wide range depending upon the mode of administration, the size and weight of the particular mammal to be treated and whether the nature of the treatment is to be prophylactic or therapeutic in nature. In general, dosage unit forms contain from about 5 mg. to about 2.0 g. of the active ingredient, administered from 1 to 4 times daily. A therapeutically effective amount of the active ingredient comprises from about 1 to about 200 mg/kg of body weight per day.

The excipients used in the preparation of the pharmaceutical compositions are those excipients which are well known in the pharmacist's art. These excipients may be either organic or inorganic, solid or liquid in nature. Suitable solid excipients include gelatin, lactose, starches, magnesium stearate and petroleum. Suitable liquid excipients include water and alcohols such as ethanol, benzyl alcohol and polyethylene alcohols either with or without the addition of a suitable surfactant. In general, the preferred liquid excipients useful, particularly for injectable preparations, include water, saline solution, dextrose and glycol solutions, such as aqueous propylene glycol or an aqueous solution of polyethylene glycol. Liquid preparations to be used as sterile injectable solutions will ordinarily contain from about 0.5% to about 25% by weight, and preferrably from about 1% to about 10% by weight, of the active ingredient in solution.

A preferred method of administration for the compounds of the present invention is perorally, either in solid dosage form such as a tablet or capsule, or in liquid form such as an oral elixer, suspension, emulsion or syrup. The tablets containing the active ingredient are mixed with a conventional inert diluent such as lactose in the presence of a disintegrating agent, e.g., maize starch, and lubricating agents such as magnesium stearate. Such tablets may, if desired, be provided with enteric coatings using methods known to those skilled in the art, as for example, the use of cellulose acetate phthalate. Similarly, either hard or soft shelled gelatin capsules, can contain a compound of formula (I), with or without additional excipients and may be prepared by conventional means. Furthermore, if desired, such capsules may conveniently contain about 25–500 mg. of the active ingredient. Other less preferred compositions for oral administration include aqueous solutions, suspensions, emulsions, or syrups. Ordinarily, the active ingredient comprises from about 0.5% to about 10% by weight in such compositions. The pharmaceutical carrier is generally aqueous in nature, as for example, aromatic water, a sugar-based syrup or a pharmaceutical mucilage. For insoluble compounds, suspending agents may also be added, as well as agents to control viscosity, as for example, magnesium aluminum silicate or carboxymethylcellulose. Buffers, preservatives, emulsifying agents and other excipients known to the art can also be added.

For parenteral administration such as intramuscular, intravenous or subcutaneous administration, the proportion of active ingredient ranges from about 0.05% to about 20% by weight and preferrably from about 0.1% to about 10% by weight of the liquid composition. In order to minimize or eliminate irritation at the site of injection, such compositions may contain a non-ionic surfactant having a hydrophile-lipophile balance (HLB) of about 12 to about 17. The quantity of surfactant in such formulations ranges from about 5% to about 15% by weight. The surfactant can be a single surfactant having the above-identified HLB or a mixture of two or more components having the desired HLB. Illustrative of surfactants useful in parenteral formulations are the class of polyoxyethylene sorbitan fatty acid esters, as for example, sorbitan monooleate, and the high molecular weight adducts of ethylene oxide with a hydrophobic base formed by the condensation of propylene oxide with propylene glycol. The concentration of active ingredient contained in these various parenteral dosage unit forms varies over a broad range and comprises from about 0.05% to about 20% by weight of the total formulation, the remaining component or components consisting of those liquid pharmaceutical excipients previously mentioned.

The invention described herein is more particularly illustrated by means of the following specific examples.

EXAMPLE 1

4-Amino-5-ethyl-4H-1,2,4-triazole-3-thiol

Thiocarbohydrazide, 212.2 grams, is added to 500 ml. of propionic acid and heated to its reflux temperature for approximately 90 minutes. The reaction mixture is cooled to room temperature and diluted with anhydrous ether. After standing overnight in the refrigerator, the desired 4-amino-5-ethyl-4H-1,2,4-triazole-3-thiol is filtered, washed with anhydrous ether and air dried to yield a product having a m.p. of 143°–6° C.

Following essentially the same procedure, but substituting acetic acid, butyric acid, isobutyric acid, valeric acid, isovaleric acid and trimethylacetic acid for the propionic acid above results in the formation of
- 4-amino-5-methyl-4H-1,2,4-triazole-3-thiol,
- 4-amino-5-propyl-4H-1,2,4-triazole-3-thiol,
- 4-amino-5-isopropyl-4H-1,2,4-triazole-3-thiol,
- 4-amino-5-butyl-4H-1,2,4-triazole-3-thiol,
- 4-amino-5-isobutyl-4H-1,2,4-triazole-3-thiol, and
- 4-amino-5-t-butyl-4H-1,2,4-triazole-3-thiol, respectively.

EXAMPLE 2

2-Bromo-5,6-dimethoxyindan-1-one

Commercially available 5,6-dimethoxyindan-1-one, 38.4 grams, contained in 250 ml. of chloroform and 50 ml. of ethyl acetate is heated to boiling. A mixture of 98.3 grams of cupric bromide and 50 ml. of ethyl acetate is added and heated to maintain the elimination of hydrogen bromide. After all of the hydrogen bromide is evolved, the mixture is heated to its reflux temperature for approximately 15 minutes, filtered and the filtrate evaporated to dryness in vacuo. The residue is dissolved in a minimum of methylene chloride, placed upon an alumina column and eluted with methylene chloride. The eluate is reduced in vacuo to a small volume, cooled, and the desired 2-bromo-5,6-dimethoxyindan-1-one when washed and air dried has a m.p. of 148°–9° C.

Following essentially the same procedure but substituting
- indan-1-one,
- 4-methylindan-1-one,
- 4,5,6-triethylindan-1-one,
- 3-butyl-5-methylindan-1-one,
- 5-isopropylindan-1-one,
- 3-ethyl-6-propoxyindan-1-one, and
- 5,6-dibutoxyindan-1-one for the
- 5,6-dimethoxyindan-1-one above, results in the formation of
- 2-bromo-indan-1-one,
- 2-bromo-4-methylindan-1-one,
- 2-bromo-4,5,6-triethylindan-1-one,
- 2-bromo-3-butyl-5-methylindan-1-one,
- 2-bromo-5-isopropylindan-1-one,
- 2-bromo-3-ethyl-6-propoxyindan-1-one, and
- 2-bromo-5,6-dibutoxyindan-1-one, respectively.

Refluxing the substituted 2-bromoindan-1-ones so obtained with a solution of sodium iodide in acetone results in the formation of the corresponding substituted 2-iodoindan-1-ones.

EXAMPLE 3

2-Bromo-4-methyl-1-tetralone

Commercially available 4-methyl-1-tetralone, 32.0 grams, contained in 250 ml. of chloroform and 50 ml. of ethyl acetate is heated to boiling. A mixture of 98.3 grams of cupric bromide and 50 ml. of ethyl acetate is heated to its reflux temperature. After all of the hydrogen bromide is evolved, the mixture is maintained at its reflux temperature for an additional hour. The reaction mixture is filtered while hot, the residue washed with boiling chloroform and the combined filtrates evaporated to dryness in vacuo. The residue is dissolved in a minimum of methylene chloride, placed upon an alumina column and eluted with methylene chloride. The eluate is concentrated and the desired 2-bromo-4-methyl-1-tetralone obtained as a dark oil.

Following essentially the same procedure but substituting
- 1-tetralone,
- 5-methyl-4-propyl-1-tetralone,
- 6,7-diethyl-1-tetralone,
- 4,5,6,7-tetramethyl-1-tetralone,
- 7-isopropyl-1-tetralone,
- 6-t-butyl-4-ethyl-1-tetralone, and
- 4,7-diethyl-1-tetralone for the
- 4-methyl-1-tetralone above, results in the formation of
- 2-bromo-1-tetralone,
- 2-bromo-5-methyl-4-propyl-1-tetralone,
- 2-bromo-6,7-diethyl-1-tetralone,
- 2-bromo-4,5,6,7-tetramethyl-1-tetralone,
- 2-bromo-7-isopropyl-1-tetralone,
- 2-bromo-6-t-butyl-4-ethyl-1-tetralone, and
- 2-bromo-4,7-diethyl-1-tetralone, respectively.

Refluxing the substituted 2-bromo-1-tetralones so obtained with a solution of sodium iodide in acetone results in the formation of the corresponding substituted 2-iodo-1-tetralones.

EXAMPLE 4

3-Ethyl-10,10a-dihydroindeno[1,2-e]-s-triazolo[3,4-b][1,3,4]thiadiazine

The compounds 2-bromo-1-indanone, 31.7 g., 4-amino-5-ethyl-1,2,4-triazole-3-thiol, 21.6 g., and 500 ml. absolute ethanol are refluxed with stirring for a period of approximately 3.5 hours. A few milliliters of methanolic hydrogen chloride are added and the reaction mixture is evaporated to dryness. The residue is dissolved in dilute hydrochloric acid and extracted with ether. The aqueous solution is made alkaline with a dilute aqueous solution of sodium hydroxide and extracted twice with methylene chloride. The methylene chloride extracts are combined, dried over anhydrous magnesium sulfate, filtered and evaporated to dryness. The crude 3-ethyl-10,10a-dihydroindeno[1,2-e]-s-triazolo[3,4-b][1,3,4]thiadiazine so obtained is recrystallized from a water-ethanol mixture to yield 21.4 grams of a product having a m.p. of 163°–4° C.

Following essentially the same procedure, but substituting 2-bromo-5,6-dimethoxy-1-indanone for the 2-bromo-1-indanone above results in the preparation of 3-ethyl-10,10a-dihydro-7,8-dimethoxy-indeno[1,2-e]-s-triazolo[3,4-b][1,3,4]thiadiazine having a m.p. of 211.5°–212.0° C.

Using essentially the same procedure, but substituting the various 2-bromoindan-1-ones of Example 2 results in the formation of the following compounds, respectively:
- 3-ethyl-10,10a-dihydro-9-methyl-indeno[1,2-e]-s-triazolo[3,4-b][1,3,4]thiadiazine,
- 3,7,8,9-tetraethyl-10,10a-dihydroindeno[1,2-e]-s-triazolo[3,4-b][1,3,4]thiadiazine,
- 10-butyl-3-ethyl-10,10a-dihydro-8-methyl-indeno[1,2-e]-s-triazolo[3,4-b][1,3,4]thiadiazine,
- 3-ethyl-10,10a-dihydro-8-isopropyl-indeno[1,2-e]-s-triazolo[3,4-b][1,3,4]thiadiazine,
- 3,10-diethyl-10,10a-dihydro-7-propoxy-indeno[1,2-e]-s-triazolo[3,4-b][1,3,4]thiadiazine, and 7,8-dibutoxy-3-ethyl-10,10a-dihydroindeno[1,2-e]-s-triazolo[3,4-b][1,3,4]thiadiazine.

EXAMPLE 5

3-Ethyl-11,11a-dihydro-10H-naphtho[1,2-e]-s-triazolo[3,4-b][1,3,4]thiadiazine

The compounds 2-bromo-1-tetralone, 33.8 grams, 4-amino-5-ethyl-1,2,4-triazole-3-thiol, 21.6 grams, and 500 ml. of absolute ethanol are refluxed with stirring for approximately 3.5 hours. The reaction mixture is evaporated, cooled and diluted with pentane. The solid material which forms on standing is filtered, washed with pentane, air dried and placed in a dilute sodium hydroxide solution. This mixture is extracted twice with methylene chloride, the organic extracts combined, washed once with water and dried over anhydrous magnesium sulfate. The anhydrous solution is filtered and the filtrate evaporated in vacuo to a small volume and diluted with pentane. The crude 3-ethyl-11,11a-dihydro-10H-naphtho[1,2-e]-s-triazolo[3,4-b][1,3,4]thiadiazine is filtered and recrystallized from a benzene-hexane solution to yield a product having a m.p. of 130°-2° C.

Following essentially the same procedure, but substituting:

2-bromo-6-methoxy-1-tetralone,
2-bromo-4-methyl-1-tetralone, and
2-bromo-5-methoxy-1-tetralone for the 2-bromo-1-tetralone above results in the formation of the following compounds, respectively:

3-ethyl-11,11a-dihydro-8-methoxy-10H-naphtho[1,2-e]-s-triazolo[3,4-b][1,3,4]thiadiazine (m.p. 125°-6° C.), 3-ethyl-11,11a-dihydro-10-methyl-10H-naphtho[1,2-e]-s-triazolo[3,4-b][1,3,4]thiadiazine (m.p. 156°-8° C.), and 3-ethyl-11,11a-dihydro-9-methoxy-10H-naphtho[1,2-e]-s-triazolo[3,4-b][1,3,4]thiadiazine (m.p. 163°-4° C.).

Using essentially the same procedure, but substituting the various 2-bromo-1-tetralones of Example 3, results in the formation of the following compounds, respectively:

3-ethyl-11,11a-dihydro-9-methyl-10-propyl-10H-naphtho[1,2-e]-s-triazolo[3,4-b][1,3,4]thiadiazine, 3,7,8-triethyl-11,11a-dihydro-10H-naphtho[1,2-e]-s-triazolo[3,4-b][1,3,4]thiadiazine, 3-ethyl-11,11a-dihydro-7,8,9,10-tetramethyl-10H-naphtho[1,2-e]-s-triazolo[3,4-b][1,3,4]thiadiazine, 3-ethyl-11,11a-dihydro-7-isopropyl-10H-naphtho[1,2-e]-s-triazolo[3,4-b][1,3,4]thiadiazine, 8-t-butyl-3,10-diethyl-11,11a-dihydro-10H-naphtho[1,2-e]-s-triazolo[3,4-b][1,3,4]thiadiazine, and 3,7,10-triethyl-11,11a-dihydro-10H-naphtho[1,2-e]-s-triazolo[3,4-b][1,3,4]thiadiazine.

EXAMPLE 6

Remission of Reserpine Induced Catalepsy Behavior

Mice of the Swiss Webster strain weighing from 18 to 25 grams each are intravenously administered 2 mg/kg of reserpine. The test compound is orally administered 60 minutes later. Observations are made 15 to 60 minutes following the administration of the test compound with respect to the motor ability of the mice. The oral $ED_{50}$ in mice for the selective remission of centrally elicited motor deficits for the compound 3-ethyl-10,10a-dihydroindeno[1,2-e]-s-triazolo[3,4-b][1,3,4]thiadiazine is approximately equal to 0.1 mg/kg. In the same test system apormorphine, which is known to be effective in the treatment of Parkinson's disease has an $ED_{50}$ of 4.6 mg/kg [P. Castargne et al., Res. Commun. Chem. Pathol. Pharmacol. 2, 154 (1971)].

EXAMPLE 7

Tablet Formulation

An illustrative preparation for tablets is as follows:

| Ingredients | Per Tablet |
|---|---|
| (a) 3-ethyl-10,10a-dihydroindeno[1,2-e]-s-triazolo[3,4-b][1,3,4]thiadiazine | 150 mg. |
| (b) Wheat starch and granulated starch paste (10% w/v) | 15 mg. |
| (c) Lactose | 33.5 mg. |
| (d) Magnesium stearate | 1.5 mg. |

The granulation obtained upon mixing lactose, starch and granulated starch paste is dried, screened and mixed with the active ingredient and magnesium stearate. The mixture is compressed into tablets weighing 200 mg. each.

EXAMPLE 8

Capsule Preparation

An illustrative preparation for hard gelatin capsules is as follows:

| Ingredients | Per Capsule |
|---|---|
| (a) 3-ethyl-11,11a-dihydro-8-methoxy-10H-naphtho[1,2-e]-s-triazolo[3,4-b][1,3,4]thiadiazine | 200 mg. |
| (b) Talc | 35 mg. |

The formulation is prepared by passing the dry powders of both (a) and (b) through a fine mesh screen and mixing them well. The mixed powders are then filled into No. 0 hard gelatin capsules at a net fill of 235 mg. per capsule.

Soft gelatin capsules can be prepared in a similar fashion. Alternatively, the talc may be omitted and the active ingredient filled directly as a granulation, slug or compressed tablet into the rotary die or plate mold in which the soft gelatin capsule is to be formed.

EXAMPLE 9

Preparation of Parenteral Formulation

An illustrative composition for a parenteral injection is the following emulsion:

| Each ml. Contains | Ingredients | Amount |
|---|---|---|
| 50 mg. | 3-ethyl-11,11a-dihydro-10H-naphtho[1,2-e]-s-triazolo[3,4-b][1,3,4]thiadiazine | 1.0 g. |
| 100 mg. | Polyoxyethylene sorbitan monooleate | 2.0 g. |
| 0.00064 mg. | Sodium chloride | 0.128 g. |
| | Water for injection, q.s. | 10 ml. |

The parenteral composition is prepared by dissolving 0.64 g. of sodium chloride in 100 ml. of water for injection, mixing the polyoxyethylene sorbitan monooleate with the 3-ethyl-11,11a-dihydro-10H-naphtho[1,2-e]-s-triazolo[3,4-b][1,3,4]thiadiazine, adding a sufficient solution of the sodium chloride in water to the active ingredient and polyoxyethylene sorbitan monooleate to bring the volume to 20 ml., shaking the mixture, and finally autoclaving the mixture for 20 minutes at 110° C., at 15 p.s.i.g. steam pressure. The composition can be dispensed either in a single ampule for subsequent use in multiple dosages or in groups of 10 and 20 ampules for a single dosage administration.

EXAMPLE 10

Preparation of an Oral Syrup

A two percent weight per volume of syrup containing 3-ethyl-10,10a-dihydro-7,8-dimethoxy-indeno[1,2-e]-s-triazolo[3,4-b][1,3,4]thiadiazine is prepared by the usual pharmaceutical techniques in accordance with the following formula:

| Ingredients | Grams |
| --- | --- |
| (a) 3-ethyl-10,10a-dihydro-7,8-dimethoxy-indeno[1,2-e]-s-triazolo[3,4-b][1,3,4]thiadiazine | 2.0 |
| (b) Sucrose | 33.0 |
| (c) Chloroform | 0.25 |
| (d) Sodium benzoate | 0.4 |
| (e) Methyl p-hydroxybenzoate | 0.02 |
| (f) Vanillin | 0.04 |
| (g) Glycerol | 1.5 |
| (h) Purified water to 100.0 ml. | |

We claim:

1. A triazolobenzocycloalkylthiadiazine having the formula

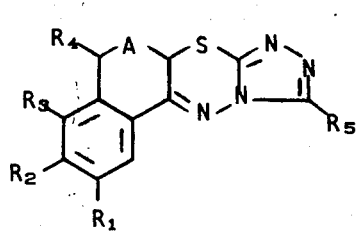

wherein
$R_1$, $R_2$, and $R_3$ are each selected from the group consisting of hydrogen, lower alkyl having from 1 to 4 carbon atoms and lower alkoxy having from 1 to 4 carbon atoms;
$R_4$ is selected from the group consisting of hydrogen and lower alkyl having from 1 to 4 carbon atoms;
A is a sigma bond or the methylene radical;
$R_5$ is lower alkyl having from 1 to 4 carbon atoms;
and the pharmaceutically acceptable acid addition salts thereof.

2. A compound according to claim 1 wherein A is a sigma bond.

3. A compound according to claim 1 wherein A is a methylene radical.

4. The compound 3-ethyl-10,10a-dihydroindeno[1,2-e]-s-triazolo[3,4-b][1,3,4]thiadiazine.

5. The compound 3-ethyl-11,11a-dihydro-8-methoxy-10H-naphtho[1,2-e]-s-triazolo[3,4-b][1,3,4]thiadiazine.

6. The compound 3-ethyl-11,11a-dihydro-10H-naphtho[1,2-e]-s-triazolo[3,4-b][1,3,4]thiadiazine.

7. A method of preparing a triazolobenzocycloalkylthiadiazine having the formula:

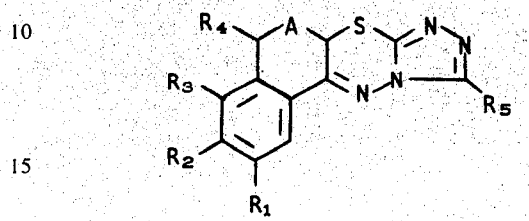

wherein $R_1$, $R_2$, and $R_3$ are each selected from the group consisting of hydrogen, lower alkyl having from 1 to 4 carbon atoms and lower alkoxy having from 1 to 4 carbon atoms; $R_4$ is selected from the group consisting of hydrogen and lower alkyl having from 1 to 4 carbon atoms; A is a sigma bond or the methylene radical; $R_5$ is lower alkyl having from 1 to 4 carbon atoms; or a pharmaceutically acceptable acid addition salt thereof; which comprises reacting a 2-halobenzocycloalkan-1-one having the formula

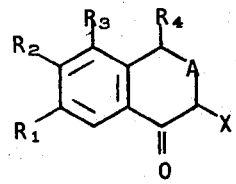

wherein $R_1$, $R_2$, $R_3$, $R_4$, and A are as defined above and X is halogen selected from the group consisting of chloro, bromo and iodo; with a 4-amino-4H-1,2,4-triazole-3-thiol having the formula

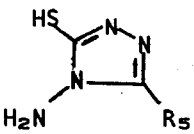

wherein $R_5$ is as defined above; reacting said ketone and said triazole at a temperature ranging from room temperature to 150° C. and for a period of time ranging from 1 to 12 hours.

8. A method of reducing depression which comprises the administration of a therapeutically effective amount of a triazolobenzocycloalkylthiadiazine of claim 1 to mammals in need thereof.

9. A method according to claim 8 in which the triazolobenzocycloalkylthiadiazine is administered in an amount of from 1 to 200 mg/kg of body weight per day.

10. A therapeutic composition in dosage unit form comprising from 5 milligrams to 2.0 grams of a compound of claim 1 and a pharmaceutical carrier.

* * * * *